United States Patent
Biskeborn et al.

(10) Patent No.: US 9,865,300 B1
(45) Date of Patent: Jan. 9, 2018

(54) MAGNETIC TAPE ABRASIVITY MEASUREMENT

(71) Applicant: INTERNATIONAL BUSINESS MACHINES CORPORATION, Armonk, NY (US)

(72) Inventors: Robert G. Biskeborn, Hollister, CA (US); Calvin S. Lo, Saratoga, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/473,811

(22) Filed: Mar. 30, 2017

(51) Int. Cl.
| | |
|---|---|
| G11B 5/187 | (2006.01) |
| G11B 20/18 | (2006.01) |
| G11B 5/39 | (2006.01) |
| G11B 5/40 | (2006.01) |
| G11B 5/008 | (2006.01) |
| G11B 5/31 | (2006.01) |
| G01R 33/12 | (2006.01) |
| G01N 3/56 | (2006.01) |
| G11B 5/455 | (2006.01) |
| G01R 27/18 | (2006.01) |

(52) U.S. Cl.
CPC ........... G11B 20/1816 (2013.01); G01N 3/56 (2013.01); G01R 27/18 (2013.01); G01R 33/1207 (2013.01); G11B 5/00813 (2013.01); G11B 5/3106 (2013.01); G11B 5/3133 (2013.01); G11B 5/3912 (2013.01); G11B 5/40 (2013.01); G11B 5/455 (2013.01)

(58) Field of Classification Search
CPC ...... G01N 3/56; G01R 33/1207; G01R 27/18; G11B 5/3106; G11B 5/3133; G11B 5/3912; G11B 5/40; G11B 5/455

USPC ........... 29/603.1; 73/7; 360/122, 125.3, 137
See application file for complete search history.

(56) References Cited

U.S. PATENT DOCUMENTS

| | | | |
|---|---|---|---|
| 3,753,093 A | 8/1973 | Gardner et al. | |
| 4,091,654 A | 5/1978 | Hurtig et al. | |
| 5,660,695 A | 8/1997 | Mahvan et al. | |
| 6,822,820 B1 * | 11/2004 | Winarski ............... | G11B 15/62 29/603.09 |
| 7,013,705 B2 | 3/2006 | Wortmann et al. | |
| 9,293,152 B2 | 3/2016 | Biskeborn et al. | |

(Continued)

OTHER PUBLICATIONS

Chou, P. et al. "Quantitative Study of Magnetic Tape Abrasivity Using Accelerated Wear Testing". Microsystem Technologies, 11, (2005) pp. 901-906.

(Continued)

Primary Examiner — Jefferson Evans
(74) Attorney, Agent, or Firm — David Zwick (57) ABSTRACT

A tape head writer yoke pole tip and a substrate ground plane are electrically coupled to the resistance measuring module. An electrically conductive wear layer is disposed over the pole tip and a ground plane at the tape bearing surface, forming a closed circuit. A magnetic tape is transported across the tape head and wears away the wear layer. The resistance measuring module identifies when the circuit becomes open, and an amount of tape travel until the open circuit occurred, and transmits this to a host computer for determination of a tape abrasivity measure as a function of the amount of tape travel. The write element can be used for write operations while the wear layer is present, and after the wear layer has been worn away.

16 Claims, 9 Drawing Sheets

(56) References Cited

U.S. PATENT DOCUMENTS

| | | | |
|---|---|---|---|
| 9,349,387 B1* | 5/2016 | Tretter | G11B 5/09 |
| 9,646,636 B2* | 5/2017 | O'Konski | G11B 5/4826 |
| 2002/0105323 A1* | 8/2002 | Sakai | G01N 27/82 |
| | | | 324/237 |
| 2004/0075940 A1* | 4/2004 | Bajorek | G11B 5/10 |
| | | | 360/110 |
| 2004/0214048 A1 | 10/2004 | Ide et al. | |
| 2005/0152055 A1* | 7/2005 | Biskeborn | G11B 5/00813 |
| | | | 360/31 |
| 2007/0109681 A1* | 5/2007 | Biskeborn | G11B 5/2652 |
| | | | 360/119.02 |
| 2007/0240295 A1 | 10/2007 | Yamada et al. | |
| 2013/0128371 A1* | 5/2013 | Brong | G11B 5/455 |
| | | | 360/31 |
| 2014/0090445 A1 | 4/2014 | Norman | |
| 2015/0380036 A1 | 12/2015 | Kasada et al. | |

OTHER PUBLICATIONS

Bhushan et al., "Measurement of Surface Topography of Magnetic Tapes by Mirau Interferometry". Applied Optics, 24(10), May 15, 1985, pp. 1489-1497.

Miyoshi et al., "Friction and Morphology of Magnetic Tapes in Sliding Contact with Nickel-Zinc Ferrite", (No. NASA-E-1720). Jan. 1984, National Aeronautic, pp. 1-19.

* cited by examiner

MAGNETIC TAPE ABRASIVITY MEASUREMENT

BACKGROUND

The present invention relates generally to the field of measuring the abrasivity of magnetic tape recording media, and more particularly, to an abrasivity measuring arrangement incorporated into a production magnetic tape head.

A problem in tape appliance technology is that there is not an easy, fast way to characterize tape recording media abrasivity, which varies among vendors, tape technology generations, production runs, etc. This is important because abrasivity is related to tape head lifetime. If tape abrasivity is too high, the tape may wear away sensitive elements in the tape head, which may damage the heads, or cause recession of the read and write elements, thus causing an increase in head tape spacing. On the other hand, if the abrasivity is too low, the tape may cause an increase in head tape spacing due to insufficient head cleaning by the tape.

BRIEF SUMMARY

An embodiment of the present invention is directed to a tape appliance that includes a tape head assembly, and a resistance measuring module. The tape head assembly includes a write element that includes a writer yoke forming pole tips at a tape bearing surface, the writer yoke being electrically coupled to the resistance measuring module, and a substrate ground plane having a portion at the tape bearing surface, the substrate ground plane being electrically coupled to the resistance measuring module. An electrically conductive wear layer is disposed over at least one of the pole tips and the portion of the ground plane at the tape bearing surface. A closed measurement circuit is formed that includes the writer yoke, the substrate ground plane, the wear layer, and the resistance measuring module. The tape appliance is operated to transport a magnetic tape medium across the tape head assembly. The resistance measuring module measures the resistance of the measurement circuit, and identifies when the measurement circuit becomes an open circuit as a result of the magnetic tape medium wearing away the wear layer. The resistance measuring module determines an amount of tape travel distance across the tape head assembly until the open circuit was detected, and transmits the determined amount of tape travel distance to a host computer for determination of a tape abrasivity measure as a function of the determined amount of tape travel. The write element included in the tape head assembly can be used for write operations while the wear layer is present over the at least one of the pole tips, and after the wear layer has been worn away by the movement of the magnetic tape medium across the tape head assembly.

Another embodiment of the invention is directed to a tape appliance that includes a tape head assembly, and a resistance measuring module. The tape head assembly includes a read element that includes a reader shield at a tape bearing surface, the reader shield being electrically coupled to the resistance measuring module, and a substrate ground plane having a portion at the tape bearing surface, the substrate ground plane being electrically coupled to the resistance measuring module. An electrically conductive wear layer is disposed over the reader shield and the portion of the ground plane at the tape bearing surface. A closed measurement circuit is formed that includes the reader shield, the substrate ground plane, the wear layer, and the resistance measuring module. The tape appliance is operated to transport a magnetic tape medium across the tape head assembly. The resistance measuring module measures the resistance of the measurement circuit, and identifies when the measurement circuit becomes an open circuit as a result of the magnetic tape medium wearing away the wear layer. The resistance measuring module determines an amount of tape travel distance across the tape head assembly until the open circuit was detected, and transmits the determined amount of tape travel distance to a host computer for determination of a tape abrasivity measure as a function of the determined amount of tape travel. The read element included in the tape head assembly can be used for read operations while the wear layer is present over the reader shield, and after the wear layer has been worn away by the movement of the magnetic tape medium across the tape head assembly.

DETAILED DESCRIPTION

In magnetic recording systems, the mechanical interaction of the magnetic head and the moving recording medium is an important factor that affects the performance and reliability of the system and lifetime of the head. A well-known way of measuring tape abrasivity uses an Al—Fe—Si (also known as "Sendust") wear bar, which may have indents to facilitate a determination of wear rate. However, this technique can be slow, difficult to perform, and can have technical shortcomings. For example, changes in the shape of the wear bar surface as it is being used can affect the wear rate being measured. The technique also relies on relatively sophisticated characterization methods to determine wear rate and thus abrasivity. In addition, the technique is based on, and thus requires, wear bars comprised of Sendust, and so is not applicable to characterizing tape abrasivity based on measuring the wear of other materials, such as ceramics.

Another common procedure for determining tape head wear is to fabricate a simulated head, to run the head for an extended period of time in operative contact with the moving magnetic tape medium, and to physically measure the wear of the simulated head. An estimate of wear that an actual production tape head would experience is then derived based on the measured wear of the simulated tape head. For example, U.S. Pat. No. 4,091,654 discloses a method for testing abrasion of a recording head. According to this patent, the smoothness of a simulated head made of polished steel or other material is measured before and after a given amount of contact with a recording medium using a fiber optic emitter/detector to measure light reflected from the surface of the head.

In another approach, a conductive wear element is deposited onto a simulated head. Electrical properties of the wear element are measured after a given amount of contact with a recording medium. For example, U.S. Pat. No. 3,753,093 discloses a device for determining the wear rate of a simulated recording head in contact with a moving magnetic tape. Strips of a magnetic alloy similar to the alloy of an actual recording head are deposited onto the surface of the simulated head. During tape transport operations, the increase of the electrical resistance of magnetic alloy strip is monitored to measure the rate of wear of the magnetic alloy strip.

In these "simulated head" approaches, the simulated heads typically replace production heads in a tape appliance, but exact production head geometries, configurations, and operating conditions may be difficult to replicate. In addition, the simulated heads are used for a finite number of abrasivity tests, and must then be replaced.

It would be advantageous to have a magnetic tape abrasivity test and measurement system that is relatively fast, is accurate and repeatable, exactly replicates the tape production operating environment, and for which the tape head does not require replacement after its usefulness for testing purposes is exhausted.

Embodiments of the invention are generally directed to a system for measuring the abrasiveness of magnetic tape recording media in a production environment. In embodiments of the invention, a wear layer comprising a thin film of a conductive material, or, in an exemplary embodiment, a conductive and non-magnetic material having negligible resistance, is deposited over the write elements of a production write head. The conductive film also is in contact with a write head substrate ground plane. In various embodiments, the each writer yoke is connected to an internal bus through a resistive element. An electrical resistance measurement module measures the resistance of a circuit that is formed by the write head substrate ground plane, the deposited conductive layer, the writer yokes, the resistive elements, and the internal bus. In an exemplary embodiment, while the wear layer remains intact, a closed circuit is formed for which the resistance in the measurement circuit is determined in accordance with the parallel resistances and tolerances for each of the resistive elements, which may also take into account the resistances and tolerances of other components in the electrical resistance measurement circuit.

As a magnetic tape media passes over the write head, for example, during a normal production workload or a during a specific testing period, the tape media wears away the thin wear layer. When the wear layer is worn away to the point that none of the writer yokes are electrically connected to the substrate ground layer via the wear layer, an open circuit occurs in the electrical resistance measurement module. The run time it takes for the magnetic tape media to wear away the wear layer to the point that an open circuit is detected by the electrical resistance measurement module provides a measure of the abrasivity of the magnetic tape media.

Advantageously, the thin deposited conductive non-magnetic wear layer does not interfere with production use of the tape head and tape appliance. Thus, tape abrasivity testing can be conducted concurrently with full production tape processing. After the tape abrasivity testing has completed, i.e., the wear layer has been worn away by the tape media, the tape head can continue to be used in full production mode, without the need to replace a simulated tape head with an actual production tape head, as is required in the prior art. Further advantageously, the environment in which tape abrasivity is tested can be an actual production environment.

Figure 1A:
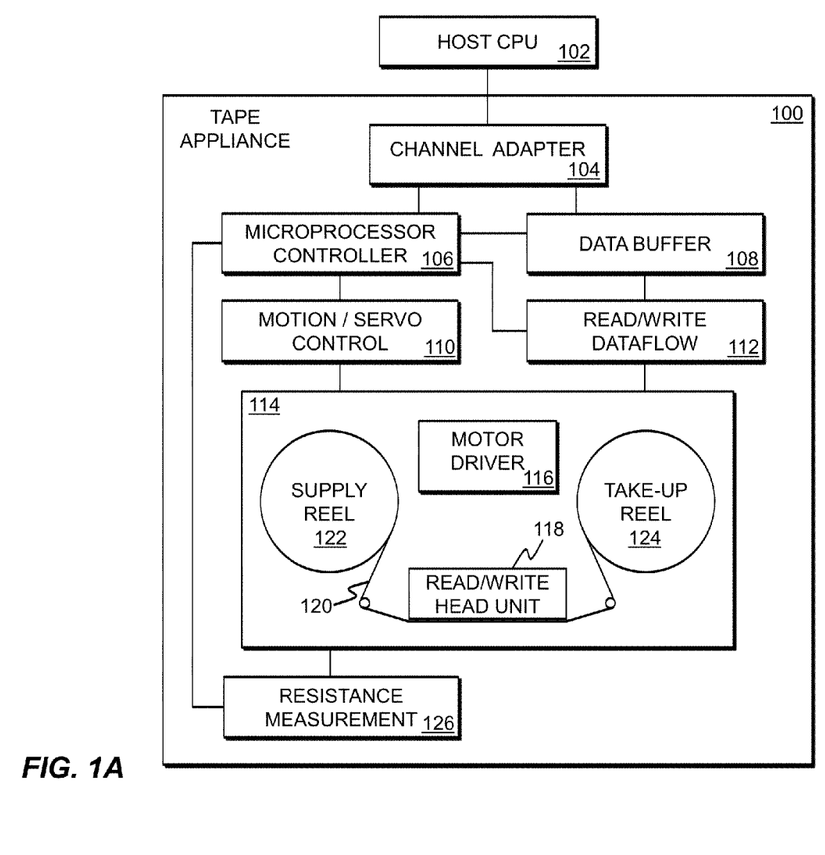
FIG. 1A is a functional block diagram illustrating a tape recording appliance, in accordance with an embodiment of the present invention.

FIG. 1 is a functional block diagram of a tape appliance 100, in accordance with an embodiment of the invention. In an exemplary embodiment, tape appliance 100 may be a production tape drive. Tape appliance 100 may include several components providing a control and data transfer system for reading and writing data from a host CPU 102, an embodiment of which is described below in relation to FIG. 7, to a magnetic tape medium 120. Tape appliance 100 may include a channel adapter 104, a computer, such as microprocessor controller 106, a data buffer 108, a read/write data flow circuit 112, a motion control system 110, a tape interface system 114 that includes a motor driver circuit 116 and read/write head unit 118, and a resistance measurement module 126.

Microprocessor controller 106 may provide overall control functionality for the operations of all other components of tape appliance 100. The functions performed by microprocessor controller 106 may be programmable via microcode routines (not shown) according to desired tape drive operational characteristics. During data write operations (with all data flow being reversed for data read operations), microprocessor controller 106 activates channel adapter 104 to perform the required host interface protocol for receiving an information data block. Channel adapter 104 communicates the data block to the data buffer 108 that stores the data for subsequent read/write processing. Data buffer 108 in turn communicates the data block received from channel adapter 104 to read/write data flow circuit 112, which formats the device data into physically formatted data that may be recorded on a magnetic tape medium. Read/write data flow circuit 112 is responsible for executing all read/write data transfer operations under the control of microprocessor controller 106. Read/write data flow circuit 112 may also control various operational aspects of tape heads. Formatted physical data from read/write data flow circuit 112 is communicated to tape interface system 114. Tape interface system 114 includes one or more read/write modules in read/write head unit 118, and drive motor components (not shown) for performing forward and reverse movement of a tape medium 120 mounted on a supply reel 122 and a take-up reel 124. The drive components of tape interface system 114 are controlled by motion control system 110 and motor driver circuit 116 to execute tape movements such as forward and reverse recording and playback, rewind and other tape motion functions. In addition, in multi-track tape drive systems, motion control system 110 transversely positions read/write heads in read/write head unit 118 relative to the direction of longitudinal tape movement in order to record data in a plurality of tracks.

In addition to the components of tape appliance 100 related to data read and write operations to tape, as described above, tape appliance 100 includes resistance measurement module 126. Resistance measurement module 126 measures the resistance of an abrasivity measurement circuit, described generally above, that includes a write head substrate ground plane, a deposited non-magnetic conductive wear layer, one or more writer yokes, and may include an internal bus connected to the writer yokes. Resistance measurement module 126 may be connected to a read/write module in read/write head unit 118 via electrical leads, and may provide data indicative of the measured resistance of the circuit to microprocessor controller 106, which may then provide the data to host CPU 102 via, for example, channel adapter 104. As described generally above, the wear layer may have negligible resistance until the layer is sufficiently worn away by the tape media to effectively cause an open circuit.

In various embodiments, based on the material and other characteristic of the wear layer, as described in more detail below, the measured resistance of the closed circuit may remain constant, within a predefined acceptable noise or fluctuation range, until the open circuit is detected, or the measured resistance may display a higher sensitivity and correlation to the thickness of the wear layer such that the measured resistance can provide a reliable indicator of wear layer thickness. In various embodiments, resistance measurement module 126 may operate similar to a digital ohm meter, and provide real-time resistance value of the abrasivity measurement circuit as the wear layer is worn away by the tape. In other embodiments, resistance measurement module 126 may operate, for example, as a bit register that contains, for example, a "1" value until on open circuit is detected in the abrasivity measurement circuit, whereupon the value in the bit register becomes "0".

In various embodiments, microprocessor controller 106 may track the total length of tape that passes over the read/write head unit 118 from initial tape appliance 100 power up, and may also track other tape movement related information, such as tape travel distance within predefined tape speed ranges. This tracked information may be periodically provided by microprocessor controller 106 to host CPU 102, at least until the wear layer is sufficiently worn away by the tape media to effectively cause an open circuit.

The total length of tape travel until an open circuit is detected by resistance measurement module 126 can be used to determine a measure of tape abrasivity. For example, a quantitative or qualitative measure of tape abrasivity can be established based, for example, on the total length of tape travel until an open circuit is detected. Alternatively, the total length of tape travel until an open circuit is detected can be correlated with other industry standard measures of tape abrasivity.

Figure 1B:
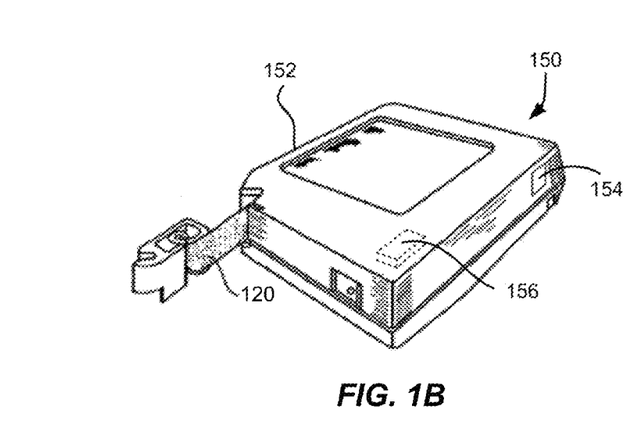
FIG. 1B illustrates an exemplary tape cartridge, in accordance with an embodiment of the present invention.

FIG. 1B illustrates an exemplary tape cartridge 150 according to an embodiment of the invention. Tape cartridge 150 may be used with a system such as tape appliance 100 shown in FIG. 1A. As shown, tape cartridge 150 includes a housing 152, a tape 120 in the housing 152, and may include a nonvolatile memory 156 coupled to the housing 152. The nonvolatile memory may be accessible by tape appliance 100, and the tape operating software (the driver software) residing on host CPU 102. In an exemplary embodiment, tape cartridge 150 meets the standards specifications of one or more of the Linear Tape Open (LTO) generations, such as LTO-7. All trademarks used herein are the property of their respective owners. In such an embodiment, supply reel 122 may be integral to the LTO tape cartridge, and the end of tape 120 includes a leader pin (not shown) which is mechanically grasped by features (not shown) of tape interface system 114 and threaded onto take-up reel 124.

While various vendors may offer LTO-compliant tape cartridges, the exact compositions of the tape media may vary by vendor and by model or part number offered by the vendor, although all may meet the standards for a particular LTO generation. While all tapes offered by a particular vendor may meet exacting standards within their model or part number, there may be variances between tapes offered by different vendors. In particular, the abrasivity of the magnetic medium layer that comes into engagement with the tape heads, for different makes and models of an LTO tape cartridge, can be different.

Figure 2:
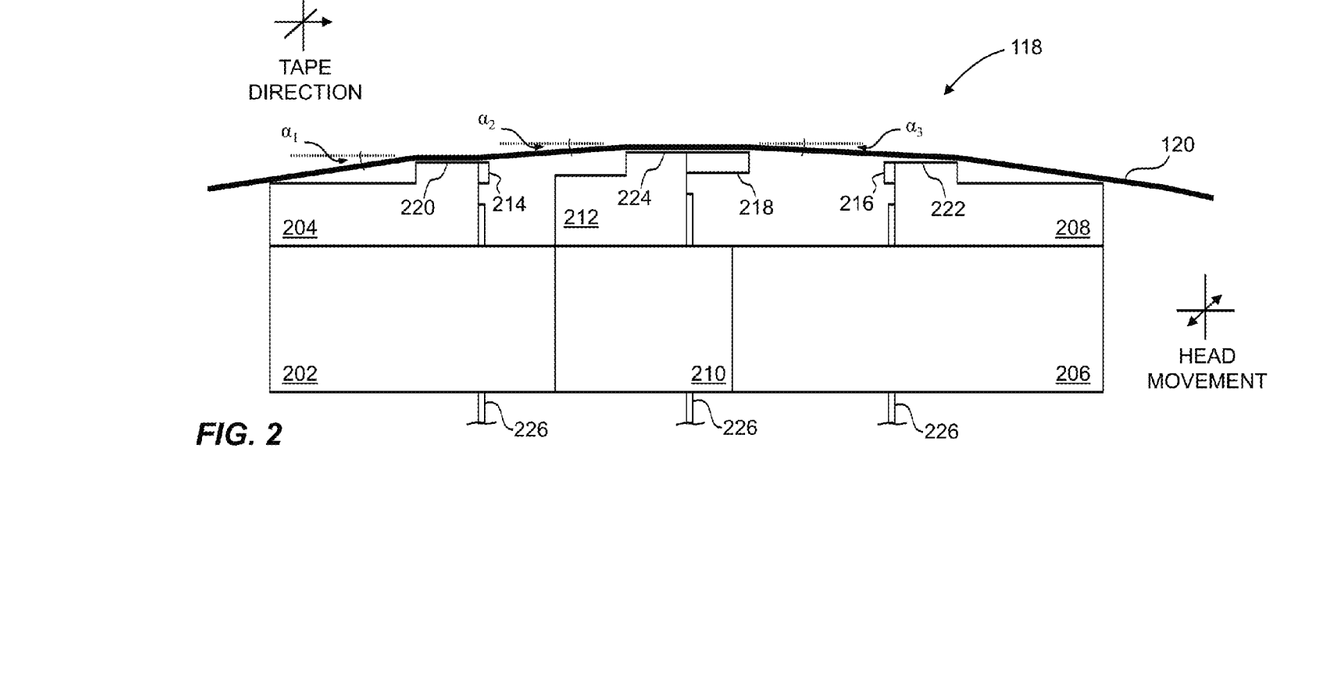
FIG. 2 illustrates a side view of a read/write head, in accordance with an embodiment of the invention.

FIG. 2 illustrates a functional schematic side view of read/write head unit 118 in accordance with an example embodiment. Read/write head 118 includes first, second and third modules 204, 212, and 208, respectively, mounted to bases 202, 210, and 206, respectively. The bases may be "U-beams" that are physically coupled together. First, second and third modules 204, 212, and 208 each have a tape bearing surface 220, 224, and 222 respectively, which may be flat, contoured, etc. Each module 204, 212, and 208 may be configured for writing and/or reading data, for example, data received from or transmitted to host CPU 102, to and from a tape 120. Modules 204, 212, 208 may receive data for writing and transmit data that is read via cables 226, which may couple the modules to read/write data flow circuit 112. Cables 226 may also connect certain structures and components in modules 204, 212, 208 related to tape abrasivity measurement to resistance measurement module 126, as will be explained in more detail below. Note that while the term "tape bearing surface" appears to imply that the surface facing tape 120 is in physical contact with the tape bearing surface, this is not necessarily the case. Rather, only a portion of the tape may be in contact with the tape bearing surface, constantly or intermittently, with other portions of the tape "flying" above the tape bearing surface on a layer of air, usually referred to as an "air bearing." By way of explanation, first module 204 can be referred to as the "leading" module as it is the first module encountered by tape 120 when moving from left to right, as illustrated. Second module 212 can be referred to as the "middle" module, and third module 208 can be referred to as the "trailing" module. The leading and trailing modules 204 and 208, respectively, may be referred to collectively as outer modules. Note that outer modules 204 and 208 will alternate as leading modules, depending on the direction of travel of the tape 120.

In an exemplary embodiment, closures 214, 218, and 216 are attached to modules 204, 212, and 208, respectively, and serve to extend tape bearing surfaces 220, 224, and 222, and to define gaps at the junctions of the modules and closures in which tape read and write elements, described in more detail below, are disposed. Locating the read and write elements interior to the edges of the tape bearing surfaces may serve to reduce wear and tear of the read/write elements resulting from direct contact from tape 120. Modules 204, 212, and 208, and closures 214, 218, and 216 may be made of a wear resistant substrate material, such as a ceramic. In some embodiments, middle module 212 has a closure, while the outer modules 204, 208 do not. Where there is no closure, preferably a hard coating is added to the module. One preferred coating is diamond-like carbon (DLC).

In the exemplary embodiment illustrated in FIG. 2, tape bearing surfaces 220, 224, and 222 of the first, second and third modules 204, 212, and 208, respectively, lie on approximately parallel planes, with tape bearing surface 224 of the middle module 212 being slightly above tape bearing surfaces 220 and 222 of the outer modules 204 and 208. As described below, this has the effect of creating a desired wrap angle $\alpha 2$ of the tape relative to the tape bearing surface 224 of the middle module 212.

Tape bearing surfaces 220 and 222 may include sharp outer edges, or "skiving" edges, where tape 120 will first contact tape bearing surfaces 220 and 222 when either outer module 204 and 208 is the leading module. The skiving edges serve to "shear" air from the underside of tape 120 to prevent air from being drawn into the head-tape gap by the tape, so that atmospheric pressure may push the tape into substantially full contact, i.e., with little or no tape fly height, over the longitudinal dimension, with respect to tape direction, of the tape bearing surfaces. A small amount of roundness or slope at the incoming edge may generate an unacceptably thick air bearing, separating the tape from the head, and its read/write elements, as described below, and present problems in reading and writing high density recordings due to spacing loss effects.

Where the tape bearing surfaces 220, 224, and 222 lie along approximately parallel offset planes, the vacuum created by the skiving edge of tape bearing surface 220 of the leading module 204 results in the trailing edge of tape bearing surface 220 (the edge from which the tape leaves the leading module 204) being the approximate reference point which defines the wrap angle α2 over the tape bearing surface 224 of the second module 212. Because the tape stays in close proximity to tape bearing surface 220 until close to its trailing, read and/or write elements, described in more detail below, may be located near the trailing, or inner, edges of the outer modules 204, 208.

A benefit of this and similar embodiments is that, because the tape bearing surfaces 220 and 222 of outer modules 204, 208 are fixed at a determined vertical offset from the tape bearing surface 224 of the middle module 212, the inner wrap angle α2 is fixed when modules 204, 212, and 208 are physically coupled together or are otherwise fixed into a head assembly. The inner wrap angle $\alpha_2$ is approximately $\tan^{-1}(\delta/W)$ where δ is the height difference between the planes of the tape bearing surfaces 220 and 224, and W is the width between the opposing ends of the tape bearing surfaces 220 and 224. An illustrative inner wrap angle $\alpha_2$ is in a range of about 0.5° to about 1.1°, though can be any angle that is advantageous to a design. Beneficially, the inner wrap angle $\alpha_2$ on the side of middle module 212 receiving the tape (leading edge) will be larger than the inner wrap angle $\alpha_3$ on the trailing edge, as the tape 120 rides above tape bearing surface 222 of trailing module 208. This difference is generally beneficial as a smaller $\alpha_3$ tends to oppose what has heretofore been a steeper exiting effective wrap angle.

Note that the tape bearing surfaces 220, 222 of the outer modules 204, 208 are positioned to achieve a negative wrap angle at the trailing edge of the tape bearing surface 220 of the leading module 204. This is generally beneficial in helping to reduce friction due to contact with the trailing edge, provided that proper consideration is given to the location of the "crowbar" region, where the tape forms a slight bubble, that forms in the tape where it peels off the head. This negative wrap angle also reduces flutter and scrubbing damage to the elements on leading module 204. Further, at trailing module 208, tape 120 flies over the tape bearing surface 222 so there is virtually no wear on the elements when tape is moving in this direction. Particularly, tape 120 entrains air and so will not significantly ride on the tape bearing surface 222 of the trailing module 208 (although some contact may occur). This is permissible in certain embodiments, for example, where the leading module writes onto the tape, the middle module may perform a read-after-write function, and the trailing module 208 is idle.

Writing and reading functions may be performed by different modules at any given time. In one embodiment, in which the modules are configured in a RWR arrangement, middle module 212 includes a plurality of write elements and optional servo readers and no read elements. Outer modules 204, 208 include a plurality of read elements and no write elements, with the exception that outer modules 204, 208 may include optional servo readers. The servo readers may be used to laterally position the head, with respect to tape direction, during reading and/or writing operations.

In the embodiment illustrated in FIG. 2, modules 204, 212, 208 each have a closure 214, 218, 216, which extends the tape bearing surface of the associated module, thereby effectively positioning the read/write elements away from the edge of the tape bearing surface. Closure 218 on second module 212 can be a ceramic closure of a type typically found on tape heads. The closures 214, 216 of the outer modules 204, 208, however, may be shorter than closure 218 of second module 212 as measured parallel to a direction of tape travel over the respective module. This enables positioning the modules closer together. One way to produce shorter closures 214, 216 is to lap the standard ceramic closures of the second module 212 an additional amount. Another way is to plate or deposit thin film closures above the elements during thin film processing. For example, a thin film closure of a hard material such as Sendust or nickel-iron alloy (e.g., 45/55) can be formed on the module.

With reduced-thickness ceramic or thin film closures 214, 216 or no closures on the outer modules 204, 208, the write-to-read gap spacing can be reduced to less than about 1 mm, e.g., about 0.75 mm, or 50% less than standard LTO tape head spacing. The open space between the modules 204, 212, 208 can still be set to approximately 0.5 to 0.6 mm, which in some embodiments is ideal for stabilizing tape motion over the second module 212.

In operation, as tape 120 passes over the read and write elements in tape bearing surfaces 220, 224, 222 of read/write head unit 118, motion control system 110 transversely positions read/write head unit 118 relative to the direction of longitudinal tape movement in order to read data from or write data to the data tracks in a particular data band of tape 120, as will be described in more detail below.

Figure 3:
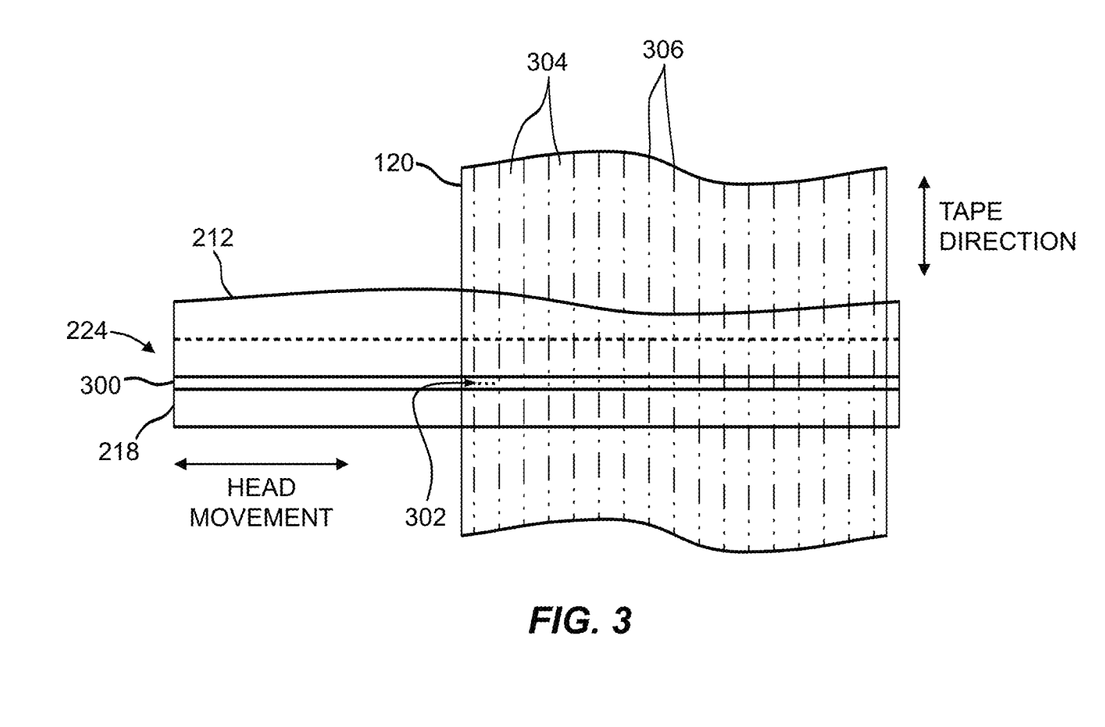
FIG. 3 illustrates a representative tape bearing surface of a module, in accordance with an embodiment of the present invention.

FIG. 3 illustrates a representative tape bearing surface 224 of module 212, from the perspective of a downward view, in accordance with an embodiment of the present invention. A representative tape 234 is shown, with servo tracks 306 indicated in dashed lines, and data bands 304 between the servo tracks 306. In this example, tape 234 includes 4 to 22 data bands 304, e.g., with 16 data bands 304 and 17 servo tracks 306, on a one-half inch wide tape 120. Each data band may include a number of data tracks, for example 1024 data tracks (not shown). Module 204 is preferably long enough to be able to support tape 234 as the head steps between data bands 304. During read/write operations, read and/or write elements of read/write element array 302, disposed in a gap 300 of tape bearing surface 224 of module 212 where the tape bearing surface of closure 218 abuts module 212, are positioned to specific track positions within one of the data bands 304. Outer read elements of read/write element array 302, which may be referred to as servo readers, read the servo tracks 306. The servo signals generated by the servo readers and received by motion control system 110 are used to align the read and/or write elements 302 with a particular set of data tracks during read/write operations.

Figure 4:
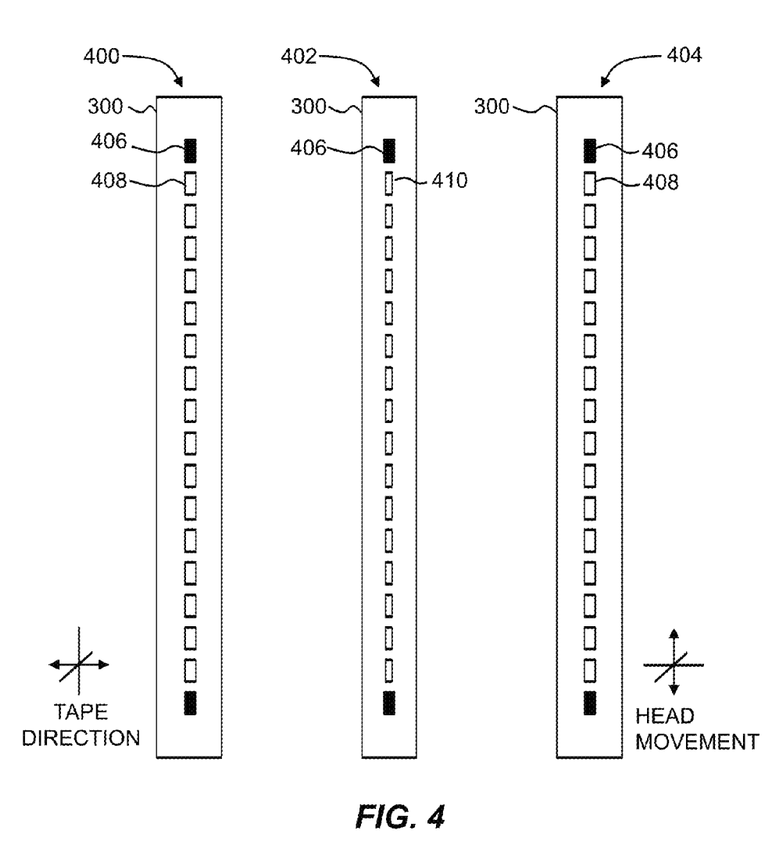
FIG. 4 illustrates read and/or write element arrays, in accordance with an embodiment of the present invention.

FIG. 4 depicts read and/or write element arrays 400, 402, and 404 of read/write head unit 118, which may be formed, for example, in gaps 300 of modules 204, 212, and 208. As shown, element arrays 400, 402, and 404 are configured and arranged in an RWR manner. The read and write element arrays may include, for example, 16 read elements 408, 16 write elements 410, and two servo readers 406, though the number of elements may vary. Various embodiments may include 8, 16, 32, 40, or 64 active read and/or write elements per array, and, alternatively, interleaved designs having odd numbers of read or write elements such as 17, 25, 33, etc. One embodiment includes 32 read elements per array and/or 32 write elements per array, where the actual number of transducer elements could be greater, e.g., 33, 34, etc. This may allow the tape to travel more slowly, thereby reducing speed-induced tracking and mechanical difficulties and/or execute fewer "wraps" to fill or read the tape. Each module 204, 212, 208 may include a complementary set of read and/or write elements for such things as bi-directional reading and writing, read-while-write capability, backward compatibility, etc.

Figure 5A:
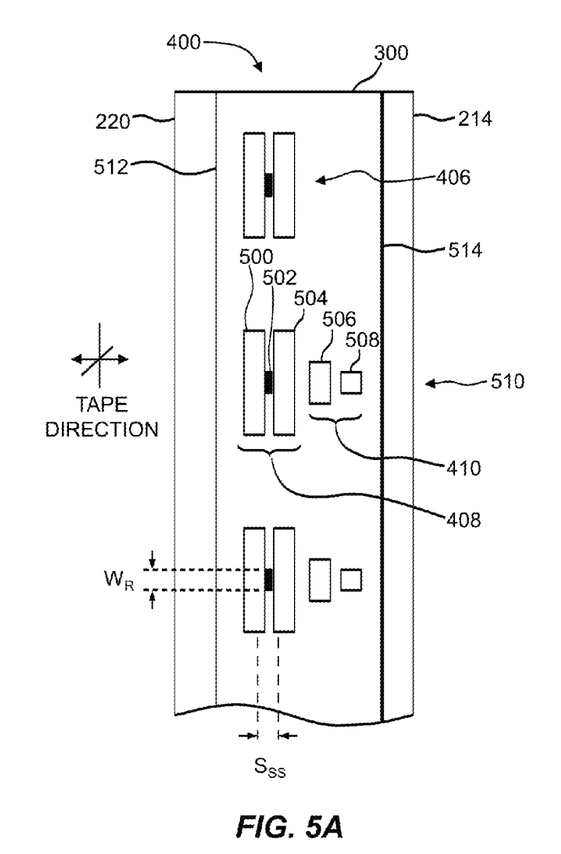
FIGS. 5A, 5B, 5C, and 5D illustrate a representative partial tape bearing surfaces, illustrating read and/or write element arrays in additional detail, in accordance with embodiments of the present invention.

FIG. 5A shows an embodiment of a partial tape bearing surface 220 of module 204 of read/write head heads 118, from the perspective of a downward view, illustrating representative read/write element array 400 in additional detail. In this embodiment, element array 400 includes both read elements and write elements. Read/write element array 400 may have a plurality of read/write element (R/W) pairs 510 in a piggyback configuration formed, for example, on the substrate material of module 204 and an optional electrically insulative layer 512. The write elements, exemplified by write element 410, and the read elements, exemplified by read element 408, are aligned parallel to the direction of travel of a tape medium to form a R/W pair 510. Several R/W pairs 510 may be present, such as 8, 16, 32 pairs, etc. The R/W pairs 510 as shown are linearly aligned in a direction generally perpendicular to the direction of tape travel. However, the pairs may also be aligned diagonally, etc. Servo readers 406 are positioned on the outside of the array of R/W pairs 510.

Generally, the magnetic tape medium may move transversely across read/write element arrays 400, 402, and 404 in either direction, and read/write heads 118 may be moved laterally, with respect to the tape direction, between data tracks and data bands 304 on the tape. The magnetic tape medium and read and/or write element arrays 400, 402, and 404 operate in a transducing relationship in a manner known in the art.

In an embodiment, when a module is constructed, for example, module 204, layers are formed in the gap 300 created above the electrically conductive substrate material of module 204 (partially shown), e.g., of AlTiC, in generally the following order for the R/W pairs 510, and similarly for servo readers 406 (however, without the writer poles): an insulating layer 512; a first reader shield 500 typically of an iron alloy such as NiFe, CZT or Al—Fe—Si (Sendust); a sensor 502 for sensing a data track on a magnetic medium of any known type, including those based on magnetoresistance (MR), giant MR (GMR), anisotropic MR (AMR), tunneling MR (TMR), etc.; a second reader shield 504 typically of a nickel-iron alloy (e.g., ~80/20 at % NiFe, also known as permalloy); a writer yoke, formed of first and second writer pole tips 506, 508, and a coil (not shown); an internal bus bar (not shown) that electrically connects the writer yokes; and a substrate ground plane 514. The writer yoke and first and second writer poles 506, 508 may be fabricated from high magnetic moment materials such as ~45/55 NiFe. Note that these materials are provided by way of example only, and other materials may be used. Additional layers such as insulation between the reader shields and/or pole tips and an insulation layer surrounding the sensor may be present. Illustrative materials for the insulation include alumina and other oxides, insulative polymers, etc.

Although read/write element array 400 includes R/W pairs 510, read/write element arrays may include only read elements or only write elements. For example, in the embodiment illustrated in FIG. 4, read/write element array 402 of module 212 includes only write elements. Other embodiments may include different combinations read/write element arrays, to enable, for example, write-read-read (W-R-R) operations, R-R-W operations, read-after-write operations, etc. One skilled in the art will appreciate that the concepts presented as applied to the embodiments disclosed would apply to configurations other than those illustrated.

In various embodiments, read sensor width $W_R$, and reader shield-to-shield spacing $S_{SS}$, as illustrated on FIG. 5, may be optimized for track density, linear density (bits/inch), head-to-tape spacing, and/or other physical and magnetic properties of a particular generation of tape, for example, LTO-7. In an exemplary embodiment, reader shield-to-shield spacing $S_{SS}$ may have a nominal value of about 100 nm, and read sensor width $W_R$ may have a nominal value of about 0.2-5.0 μm. More generally, the reader shield-to-shield spacing $S_{SS}$ scales with the bit length, as is known in the art, and the reader width may be in the range of 40-80 percent of the track width.

Figure 5B:
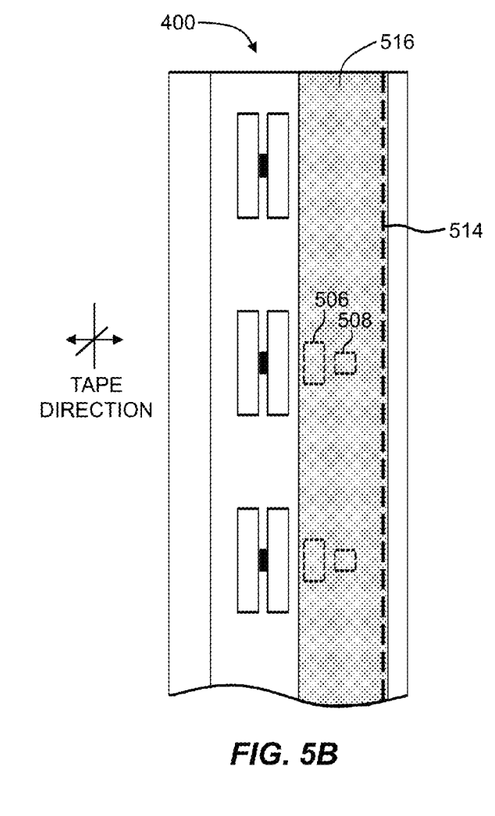

FIG. 5B shows the representative partial tape bearing surface 220 of FIG. 5A, with the addition of a wear layer 516. As generally described above, wear layer 516 is formed of a thin film of non-magnetic electrically conductive material that may be deposited, or otherwise disposed, on tape bearing surface 220 so as to cover, and thus electrically connect, substrate ground plane 514 with the writer pole tips 506 and 508. and thus their writer yokes.

In various embodiments, the non-magnetic electrically conductive material may be formed of a metal, such as Ti, Ta, Al, Au, Jr, Ru, W, Mo; alloys, including NiFe, alfesil, CZT; conducting ceramics; conductive nitrides, such as TiN, ZrN; conductive borides; conductive carbides; etc. The thickness of the may range from, for example, 2 nm to 50 nm. In various embodiments, the thickness of the wear layer may be constant, or vary along its longitudinal length.

Generally, wear layer 516 can be any suitable non-magnetic material with conductive properties as required by various embodiments, deposited onto tape bearing surface 220 in any suitable manner and at any suitable thickness, such that the wear layer will allow for tape processing at a suitable write quality level, will wear away as a result of tape abrasivity within a suitable time period, as may be determined as a design choice, will not cause damage to the read/write modules beyond an acceptable amount, and will not cause damage to the magnetic tape beyond an acceptable amount. In various embodiments, the conductive properties of wear layer 516 may be such that, in practice, the electrical resistance is negligible until a gap across the layer occurs as a result of the tape wearing away the layer, upon which an open circuit occurs. In other embodiments, the wear layer may exhibit a more easily measured increase in electrical resistance as a function of the remaining thickness of the layer as the tape wears away the layer. For example, the resistance of the measurement circuit maybe an increasing monotonic function inversely proportional to the remaining thickness of the wear layer as the layer is worn away by the magnetic tape medium as the magnetic tape medium is transported across the head assembly. The particular choice of the wear layer material, and associated dimensions, such as layer thickness and size and shape on the tape bearing surface 220, is a design decision.

Figure 5C:
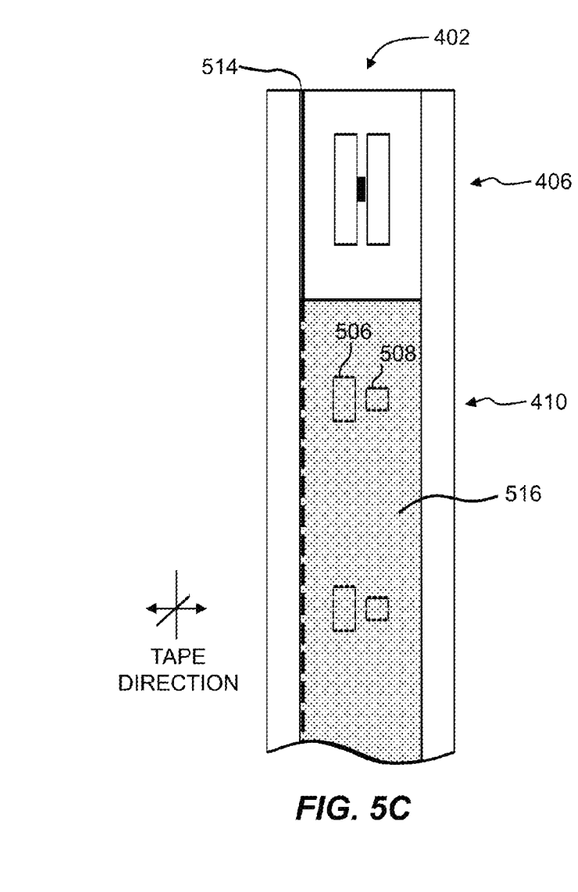

FIG. 5C shows an embodiment of a partial tape bearing surface 220 of module 204 in which the module only includes write elements 410, along with one or more servo readers 406. In this embodiment, wear layer 516 is disposed on the tape bearing surface so as to cover and electrically connect pole tips 506 and 508, and substrate ground plane 514.

Figure 5D:
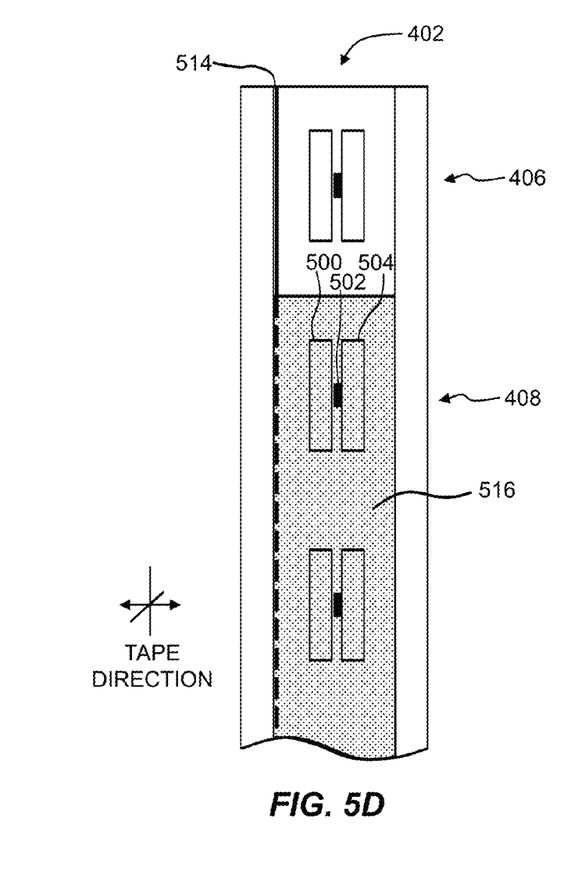
Figure 7:
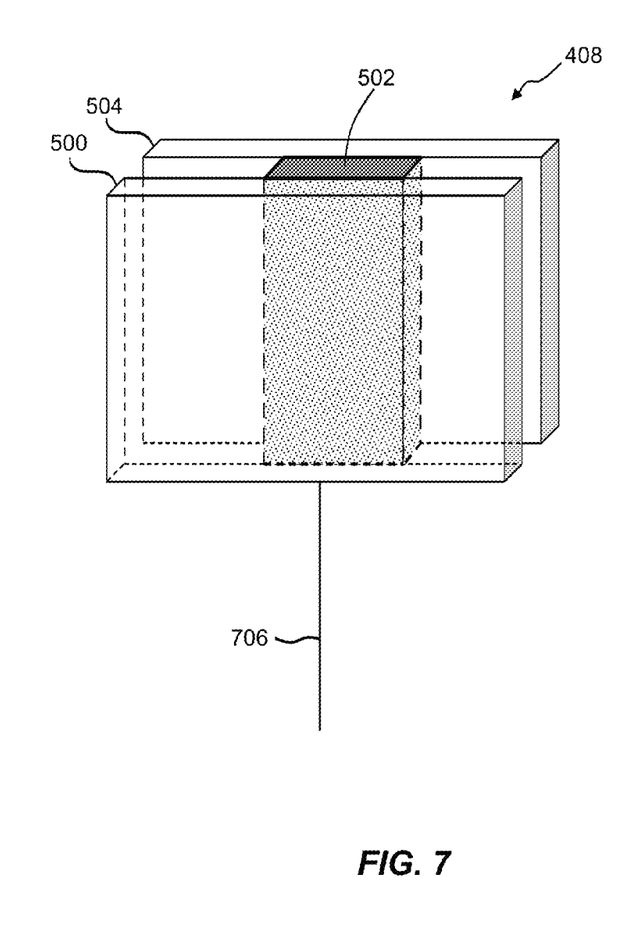
FIG. 7 illustrates a solid view of a read element, in accordance with an embodiment of the invention.

FIG. 5D shows an embodiment of a partial tape bearing surface 220 of module 204 in which the module only includes read elements 408, along with one or more servo readers 406. In this embodiment, wear layer 516 is disposed on the tape bearing surface so as to cover and electrically connect reader shields 500 and 504, and substrate ground plane 514. As illustrated in FIG. 7, in one embodiment, only one of the reader shields, for example, first reader shield 500, forms part of the abrasivity measurement circuit.

Figure 6A:
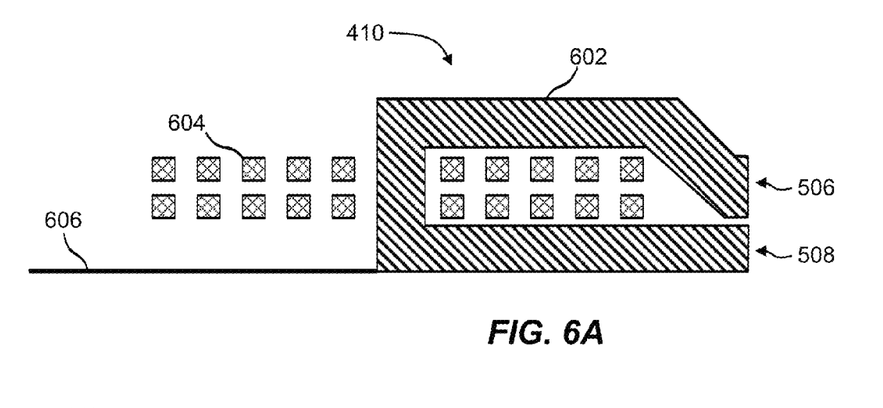
FIGS. 6A and 6B illustrate cross sectional views of a write element, in accordance with an embodiment of the invention.
Figure 6B:
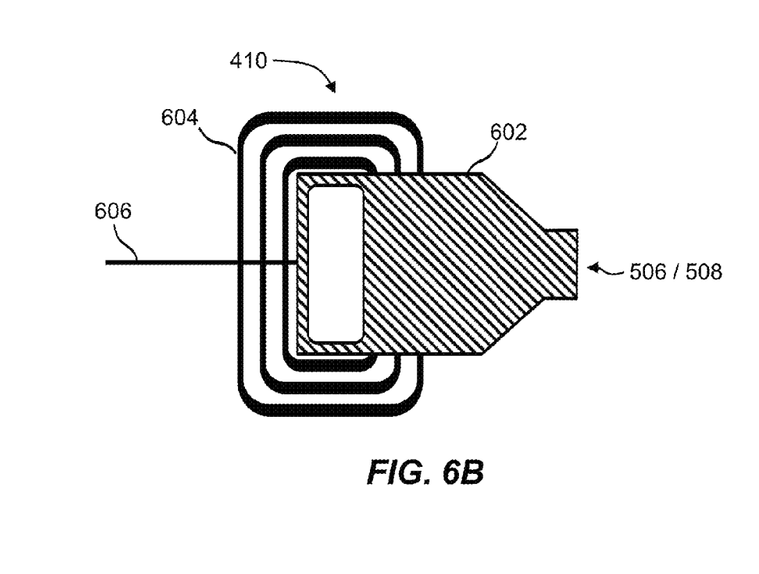

FIG. 6A is a cross sectional view of a portion of a write element 410 taken along a plane perpendicular to the tape bearing surface in which pole tips 506 and 508 of writer yoke 602 engage a tape, and perpendicular to coils 604 of the writ element. FIG. 6B is a cross sectional view of a portion of write element 410 taken along a plane perpendicular to the tape bearing surface, with the plane rotated 90 degrees so as to be parallel to the plane of coils 604. Of note in FIGS. 6A and 6B is electrical trace 606, which connects writer yoke 602 to resistance measurement module 126. In various embodiments, each electrical trace 606 for each write element may connect to an internal bus of the write element 410. In certain embodiments, a resistive element, for example, a 25 kΩ resistor element, may be present in the electrical connections between the writer yokes and the internal bus. The internal bus may connect, for example, to cables 226, which may then be coupled to resistance measurement module 126.

FIG. 7 is an isometric view of a read element 408, in accordance with an embodiment of the invention. As shown, sensor 502 is disposed between first reader shield 500 and second reader shield 504. A trace 706, is connected to one or both of the reader shields, and is then coupled to resistance measurement module 126. In the illustrated embodiment, trace 706 couples first reader shield 500 to resistance measurement module 126. In certain embodiments, a resistive element, for example, a 25 kΩ resistor element, may be present in the electrical connection between the resistance measurement module 126 and each of the reader shields connected to the resistance measurement module.

Figure 8:
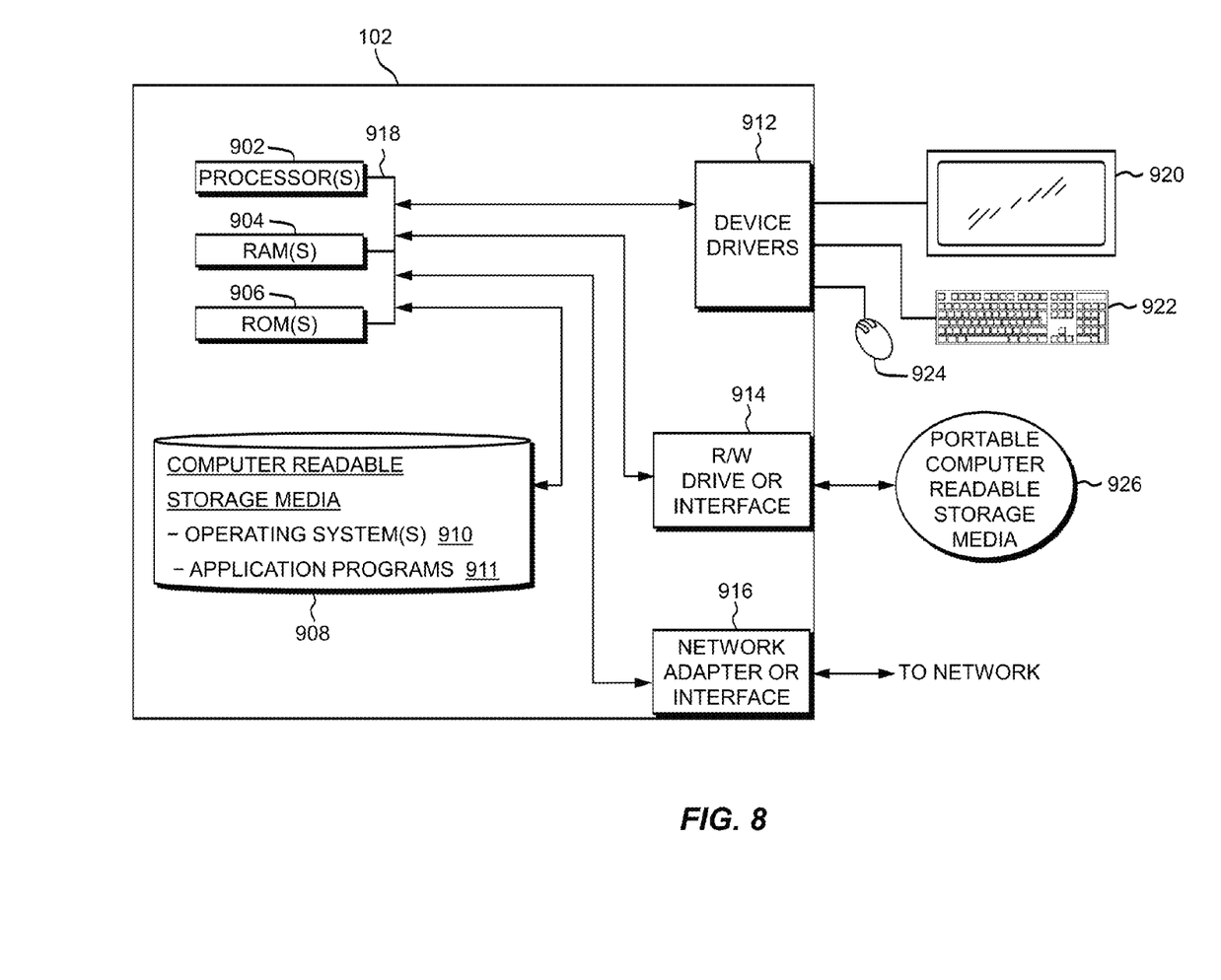
FIG. 8 illustrates a block diagram of components of a host computer, in accordance with an embodiment of the present invention.

FIG. 8 depicts a block diagram of components of host CPU 102, in accordance with an embodiment of the present invention. It should be appreciated that FIG. 7 provides only an illustration of one implementation and does not imply any limitations with regard to the environments in which different embodiments may be implemented. Many modifications to the depicted environment may be made.

Host CPU 102 can include one or more processors 902, one or more computer-readable RAMs 904, one or more computer-readable ROMs 906, one or more computer-readable storage media 908, device drivers 912, read/write drive or interface 914, network adapter or interface 916, all interconnected over a communications fabric 918. Communications fabric 918 can be implemented with any architecture designed for passing data and/or control information between processors (such as microprocessors, communications and network processors, etc.), system memory, peripheral devices, and any other hardware components within a system.

One or more operating systems 910 and application program(s) 928 are stored on one or more of the computer-readable storage media 908 for execution by one or more of the processors 902 via one or more of the respective RAMs 904 (which typically include cache memory). In the illustrated embodiment, each of the computer-readable storage media 908 can be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Host CPU 102 can also include a R/W drive or interface 914 to read from and write to one or more portable computer-readable storage media 926. Application program(s) 928 on host CPU 102 can be stored on one or more of the portable computer-readable storage media 926, read via the respective R/W drive or interface 914 and loaded into the respective computer-readable storage media 908.

Host CPU 102 can also include a network adapter or interface 916, such as a TCP/IP adapter card or wireless communication adapter (such as a 4G wireless communication adapter using OFDMA technology). Application program(s) on host CPU 102 can be downloaded to the computing device from an external computer or external storage device via a network (for example, the Internet, a local area network or other, wide area network or wireless network) and network adapter or interface 916. From the network adapter or interface 916, the programs are loaded into the computer-readable storage media 908. The network may comprise copper wires, optical fibers, wireless transmission, routers, firewalls, switches, gateway computers and/or edge servers.

Host CPU 102 can also include a display screen 920, a keyboard or keypad 922, and a computer mouse or touchpad 924. Device drivers 912 interface to display screen 920 for imaging, to keyboard or keypad 922, to computer mouse or touchpad 924, and/or to display screen 920 for pressure sensing of alphanumeric character entry and user selections. The device drivers 912, R/W drive or interface 914 and network adapter or interface 916 can comprise hardware and software (stored in computer-readable tangible storage device 908 and/or ROM 906).

In various embodiments, host computer 102 may receive data, information, and/or other signals from microprocessor 106, via, for example, network adapter or interface 916, resulting from signals received by the microprocessor from resistance measurement module 126. The received data and/or information may be stored on computer readable storage media 908. An application program, for example, one of application programs 911, may process the received data, information, and/or other signals, and determine a measure of tape abrasivity, which may be reported out, for example, onto display screen 920.

Based on the foregoing, numerous embodiments of a system to measure tape abrasivity have been disclosed. However, numerous modifications and substitutions can be made without deviating from the scope of the present invention. Therefore, the present invention has been disclosed by way of example and not limitation.

What is claimed is:

1. A tape appliance comprising:
   a tape head assembly; and
   a resistance measuring module;
   wherein the tape head assembly comprises a write element that includes:
   a writer yoke forming pole tips at a tape bearing surface, the writer yoke being electrically coupled to the resistance measuring module;
   a substrate ground plane having a portion at the tape bearing surface, the substrate ground plane being electrically coupled to the resistance measuring module;

an electrically conductive wear layer disposed over at least one of the pole tips and the portion of the ground plane at the tape bearing surface;

whereby a closed measurement circuit is formed that includes the writer yoke, the substrate ground plane, the wear layer, and the resistance measuring module;

the tape appliance operated to:
transport a magnetic tape medium across the tape head assembly;
measure, by the resistance measuring module, the resistance of the measurement circuit;
identify, by the resistance measuring module, when the measurement circuit becomes an open circuit as a result of the magnetic tape medium wearing away the wear layer;
determine an amount of tape travel distance across the tape head assembly until the open circuit was detected; and
transmit the determined amount of tape travel distance to a host computer for determination of a tape abrasivity measure as a function of the determined amount of tape travel;
whereby the write element included in the tape head assembly can be used for write operations while the wear layer is present over the at least one of the pole tips, and after the wear layer has been worn away by the movement of the magnetic tape medium across the tape head assembly.

2. The tape appliance of claim 1, wherein the tape head assembly further comprises an internal bus, each of a plurality of write elements is electrically connected to the internal bus via their writer yokes and a corresponding plurality of resistive elements, and the internal bus is electrically coupled to the resistance measuring module.

3. The tape appliance of claim 2, wherein the resistive element is a 25 kΩ resistor element.

4. The tape appliance of claim 1, wherein the wear layer is formed from a material selected from the group consisting of: Ti, Ta, Al, Au, Ir, Ru, W, Mo, NiFe, alfesil, CZT, TiN, ZrN, conducting ceramics, conductive nitrides; conductive borides; and conductive carbides.

5. The tape appliance of claim 1, wherein the wear layer is a non-magnetic electrically conductive wear layer.

6. The tape appliance of claim 1, wherein the wear layer has a thickness in the range 2 nm to 50 nm.

7. The tape appliance of claim 1, wherein the resistance of the measurement circuit is constant, within a predefined acceptable noise or fluctuation range, until an open circuit is caused by the magnetic tape medium wearing away the wear layer.

8. The tape appliance of claim 1, wherein the resistance of the measurement circuit is an increasing monotonic function inversely proportional to the remaining thickness of the wear layer as the layer is worn away by the magnetic tape medium as the magnetic tape medium is transported across the head assembly.

9. A tape appliance comprising:
a tape head assembly; and
a resistance measuring module;
wherein the tape head assembly comprises a read element that includes:
a reader shield at a tape bearing surface, the reader shield being electrically coupled to the resistance measuring module;
a substrate ground plane having a portion at the tape bearing surface, the substrate ground plane being electrically coupled to the resistance measuring module;
an electrically conductive wear layer disposed over the reader shield and the portion of the ground plane at the tape bearing surface;
whereby a closed measurement circuit is formed that includes the reader shield, the substrate ground plane, the wear layer, and the resistance measuring module;
the tape appliance operated to:
transport a magnetic tape medium across the tape head assembly;
measure, by the resistance measuring module, the resistance of the measurement circuit;
identify, by the resistance measuring module, when the measurement circuit becomes an open circuit as a result of the magnetic tape medium wearing away the wear layer;
determine an amount of tape travel distance across the tape head assembly until the open circuit was detected; and
transmit the determined amount of tape travel distance to a host computer for determination of a tape abrasivity measure as a function of the determined amount of tape travel;
whereby the read element included in the tape head assembly can be used for read operations while the wear layer is present over the reader shield, and after the wear layer has been worn away by the movement of the magnetic tape medium across the tape head assembly.

10. The tape appliance of claim 9, wherein the reader shield is electrically coupled to the resistance measuring module through a resistive element.

11. The tape appliance of claim 10, wherein the resistive element is a 25 kΩ, resistor element.

12. The tape appliance of claim 9, wherein the wear layer is formed from a material selected from the group consisting of: Ti, Ta, Al, Au, Ir, Ru, W, Mo, NiFe, alfesil, CZT, TiN, ZrN, conducting ceramics, conductive nitrides; conductive borides; and conductive carbides.

13. The tape appliance of claim 9, wherein the wear layer is a non-magnetic electrically conductive wear layer.

14. The tape appliance of claim 9, wherein the wear layer has a thickness in the range 2 nm to 50 nm.

15. The tape appliance of claim 9, wherein the resistance of the measurement circuit is constant, within a predefined acceptable noise or fluctuation range, until an open circuit is caused by the magnetic tape medium wearing away the wear layer.

16. The tape appliance of claim 9, wherein the resistance of the measurement circuit is an increasing monotonic function inversely proportional to the remaining thickness of the wear layer as the layer is worn away by the magnetic tape medium as the magnetic tape medium is transported across the head assembly.

* * * * *